US011846989B1

(12) United States Patent
Edwards (10) Patent No.: US 11,846,989 B1
(45) Date of Patent: *Dec. 19, 2023

(54) TRACKING WRISTBAND

(71) Applicant: Shari L. Edwards, Los Angeles, CA (US)

(72) Inventor: Shari L. Edwards, Los Angeles, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/446,433

(22) Filed: Aug. 8, 2023

Related U.S. Application Data

(63) Continuation of application No. 18/190,280, filed on Mar. 27, 2023, now Pat. No. 11,762,424, which is a continuation of application No. 18/171,463, filed on Feb. 20, 2023, which is a continuation of application No. 17/937,414, filed on Sep. 30, 2022, now Pat. No. 11,609,608, which is a continuation of application No. 17/845,917, filed on Jun. 21, 2022, now Pat. No. 11,460,886, which is a continuation of application No. 17/681,556, filed on Feb. 25, 2022, now Pat. No. 11,379,003, which is a continuation of application No. 17/477,441, filed on Sep. 16, 2021, now Pat. No. 11,275,407, which is a continuation of application No. 17/323,932, filed on May 18, 2021, now Pat. No. 11,132,022.

(60) Provisional application No. 63/035,114, filed on Jun. 5, 2020.

(51) Int. Cl.
*G06F 1/16* (2006.01)
*G16H 10/65* (2018.01)
*A44C 5/00* (2006.01)
*G06K 19/06* (2006.01)
*G06Q 50/26* (2012.01)

(52) U.S. Cl.
CPC ............ *G06F 1/163* (2013.01); *A44C 5/0015* (2013.01); *G06K 19/06037* (2013.01); *G06Q 50/26* (2013.01); *G16H 10/65* (2018.01)

(58) Field of Classification Search
CPC . G06F 1/163; A44C 5/0015; G06K 19/06037; G16H 10/65
See application file for complete search history.

(56) References Cited

U.S. PATENT DOCUMENTS

| | | | |
|---|---|---|---|
| 11,132,022 B2 * | 9/2021 | Edwards | ................. G06F 1/163 |
| 11,221,651 B2 | 1/2022 | Edwards | |
| 11,275,407 B2 * | 3/2022 | Edwards | .......... G06K 19/06037 |
| 11,379,003 B2 * | 7/2022 | Edwards | ................. G16H 10/65 |
| 11,460,886 B1 * | 10/2022 | Edwards | ................. G16H 50/80 |
| 11,567,536 B1 | 1/2023 | Edwards | |
| 11,609,608 B2 | 3/2023 | Edwards | |
| 11,762,424 B2 * | 9/2023 | Edwards | .......... G06K 19/06037 361/679.03 |

(Continued)

*Primary Examiner* — Matthew Mikels
(74) *Attorney, Agent, or Firm* — Steinfl + Bruno LLP (57) ABSTRACT

A method to track an individual wearing a battery-operated wearable and lockable tracking device. An identification number is provided on the tracking device or separately from the tracking device and remotely stored. Device location information about the tracking device is received from the location tracker. Based on the location information received, a determination is made whether the individual is potentially subject to a condition. In such case, the device location is tracked, and the individual is wirelessly alerted and tracked. Upon tracking, the individual is identified.

14 Claims, 5 Drawing Sheets

(56) References Cited

U.S. PATENT DOCUMENTS

2023/0205267 A1 6/2023 Edwards
2023/0236630 A1 7/2023 Edwards

* cited by examiner

TRACKING WRISTBAND

CROSS REFERENCE TO RELATED APPLICATIONS

The present application is a continuation application of U.S. Non-Provisional application Ser. No. 18/190,280 filed on Mar. 27, 2023, which, in turn, is a continuation of U.S. Non-Provisional application Ser. No. 18/171,463 filed on Feb. 20, 2023, which in turn, is a continuation of U.S. Non-Provisional application Ser. No. 17/937,414 filed Sep. 30, 2022, now U.S. Pat. No. 11,609,608, which in turn, is a continuation of U.S. Non-Provisional application Ser. No. 17/845,917 filed Jun. 21, 2022, now U.S. Pat. No. 11,460,886, which, in turn, is a continuation application of U.S. Non-Provisional application Ser. No. 17/681,556, filed Feb. 25, 2022, now U.S. Pat. No. 11,379,003, which, in turn, is a continuation application of U.S. Non-Provisional application Ser. No. 17/477,441, filed on Sep. 16, 2021, now U.S. Pat. No. 11,275,407, which, in turn, is a continuation application of U.S. Non-Provisional application Ser. No. 17/323,932, filed on May 18, 2021, now U.S. Pat. No. 11,132,022, which, in turn, claims priority to U.S. Provisional Application Ser. No. 63/035,114, filed Jun. 5, 2020, the contents of all of which are incorporated herein by reference in their entirety.

FIELD

The present disclosure relates to a tracking wristband and related methods of use.

BACKGROUND

With the current global coronavirus (COVID-19) pandemic taking almost 600,000 lives in the United States and more than 3 million lives globally, time is of the essence to develop a unified global plan, as well as a coordinated plan within each country.

There have been various attempts to track, trace, and contact individuals. Currently, the turnaround time and related processing, mostly based on phone communications, is of too many human hours, with an average waiting time of about a week to contact those that have been exposed. Using the old-fashioned-way to track, trace, and contact everyone represents a nearly impossible task.

As a consequence, there is a need for a technical solution that tracks everyone without risking their privacy and allows contacting everyone that has been exposed faster than the current several human hours. Ability to track, trace, and contact individuals accurately and completely has become a necessary requirement.

SUMMARY

The tracking and passport device according to the present disclosure provides a technical solution to help end the global pandemic for the United States and globally.

Advantageously, such tracking device and passport does more than just tracking and tracing, it can be used to potentially contact anyone exposed on the same day a positive test result occurs.

The solution presented through the herein described pandemic wristband is to be preferred to the use of cell phones as such. Using cell phones risks privacy and it is likely that a high percentage of individuals will not opt in, due to the ability of personal cell phones to be used as a means to track people. Using cell phones would likely provide an unreliable reading, as only a limited number of users will adopt a new technology, not to mention the fact that many people do not own cell phones, or carry them at all times.

While the use of the present pandemic wristband is currently targeted with reference to COVID-19, the person skilled in the art will understand that the wristband may be used for any type of pandemics. In particular, with any kind of pandemic, if immunity can be obtained from a disease, virus and/or infection through e.g. a vaccine, the green light provided by the device according to the present disclosure will be suitable for being used as a passport for the purpose not only of travel, but also acceptance to social gathering places and events such as restaurants, gyms, stores, entertainment and so on.

According to a first aspect, a wearable computing medical tracking and passport device is described, comprising: a main body including a QR code, a first indicator light and a second indicator light; a location tracker in the main body configured to transmit device location of the computing device; a processor in the main body configured to process and wirelessly receive information, and a wristband coupled to the main body, the computing device being configured to: i) illuminate, through the processor, the first indicator light when the user has been exposed to a pandemic disease; and ii) illuminate, through the processor, the second indicator light when the user is immune from the pandemic disease.

According to a second aspect, a wearable computing medical tracking and passport device is described, comprising: a main body including an indicator light and a QR code; a location tracker in the main body configured to transmit device location of the computing device; and, a processor in the main body configured to process and wirelessly receive information, the computing device being configured to: illuminate, through the processor, the indicator light with a first color when the user has been exposed to a pandemic disease and illuminate, through the processor, the indicator light with a second color when the user is immune from the pandemic disease.

In accordance with the teachings of the present disclosure, the only information that is not user-provided is the user's name and address. All other information can be provided at the user's discretion and control and can also be changed in time. In this way, any privacy concerns are well addressed and customized on a user-by-user basis.

Given that the effectiveness of the tracking, tracing and contacting system described in the present application is a function of the number of users wearing the pandemic wristband, use of such wristband may become mandatory before a COVID-19 (or other kind of pandemic) test is administered if so desired by a local and/or federal authority.

The teachings of the present disclosure will allow the use of a coordinated statewide, national, and global plan to help in Phase 4 (i.e. when shutdown will be lifted) and to help the pandemic through tracking, tracing, contacting and passport indication to show immunity. The device according to the present disclosure provides a non-discriminating way to help everyone as it is configured to reach everyone equally and can give priority testing equally.

DETAILED DESCRIPTION

The medical tracking device and passport according to the present disclosure is intended for positive use in helping every single person that wears it. The wristband is preferably waterproof and locks on the user's wrist like a hospital bracelet. If desired or required, the wristband can be designed to be removable. In such case, the wristband fastening would operate similarly to a sports band, thus also allowing the wristband to be removed when needed from children if deemed necessary. Having a pandemic wristband that locks on like a hospital bracelet until cut off would give more validity to the data and solution this would provide.

Figure 1:
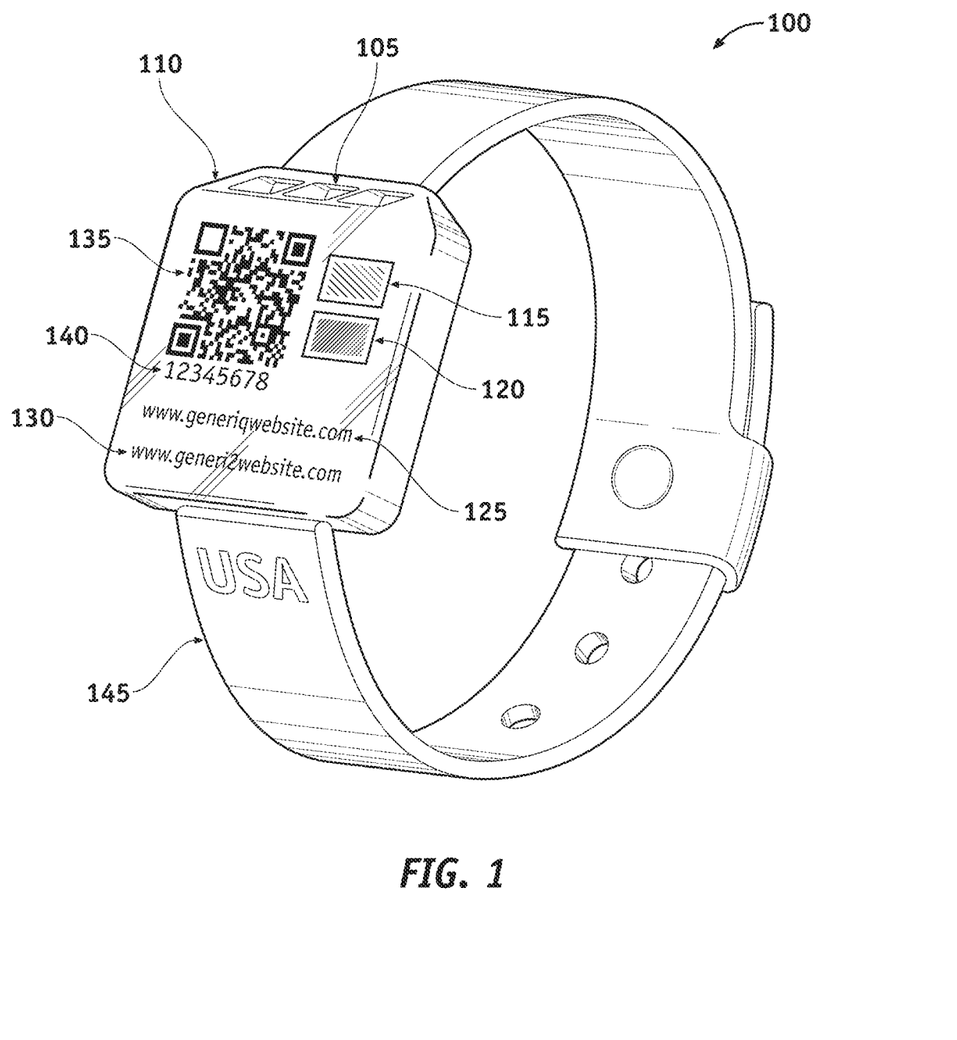
FIG. 1 shows a schematic view of the digital tracking and passport device of the disclosure, inclusive of a wristband and a screen.

FIG. 1 shows an embodiment of the pandemic wristband (100) according to the present disclosure, provided by way of example and not of limitation.

A watch face (110) is located on top of a wristband (145). The face (110) includes a first section (135) for showing a QR code for scanning purposes, a second section (140) under the first section showing an identification (ID) number, a third section (115, 120) to the right of the first section showing red (115) and green (120) lights respectively, and a fourth section (125, 130) under the ID number (140) to show website information. According to an embodiment of the present disclosure, presence of a red light indicates occurred exposure of the user and necessity for priority testing. The green light indicates immunity.

The device further includes a location tracker, such as a GPS device, together with wireless adapter for Wi-Fi® and/or Bluetooth® connectivity. The combination of the location tracker and wireless adapter allows tracking information about the location of the user to be sent, for example, to a repository at a remote location and be saved for at least a predetermined amount of time.

The red light indicator (115) is normally in an OFF state. According to the present disclosure, as soon as an individual has tested positive for a pandemic such as COVID-19, the related information is communicated to the repository. By way of example and not of limitation, such information can be input locally at the facility where the individual was tested if applicable, or where the results are obtained, or simply mailed out to the repository. Upon receipt at the repository, the stored location information of the individual will be reviewed (preferably by means of software for fast track, trace, and contact, or alternatively by human, if desired) in order to allow retrieval of the ID numbers of any wristband wearer that was within a certain distance from the diagnosed individual. As soon as such ID numbers are traced and identified, a contacting signal is sent to all the individuals identified by such ID numbers to automatically turn the red light (115) ON and provide additional information through one or more website URLs in sections (125, 130). Such URL sections can provide information both for device initialization purposes and for testing location indication, as also explained later, to help exposed individuals find a convenient location to go to for priority testing and potentially prepare for quarantine. If desired, the red light indicator (115) can also optionally briefly flash at predetermined intervals. The flashing would stop as soon as testing occurs. Alternatively, the flashing could just start and stop at predetermined or random intervals.

In other words, the red light indicator (115) indicates exposure in case the user has come in contact or proximity to people that have tested positive. If desired, the device may also include a vibrating arrangement to alert the user if visually impaired. The website URLs contain relevant information for testing purposes and/or required isolation. The exposed individuals will be able to go online and type in their ID number to find a convenient location to go to for priority testing and potentially prepare for quarantine. In this respect, the information encoded in the device through the QR code (135) may be easily read/scanned at testing sites, medical facilities, shelters, or additional allocated locations, through already existing technology.

Turning now to the green light indicator (120), such indicator is automatically activated (turned ON) by the overseeing authority once it is determined that immunity i) after recovery from COVID-19 or any other pandemic has been persistent for a determined amount of time (e.g. 1 month) or ii) after a sufficient amount of time has passed after vaccination (e.g. 2 weeks after the first shot for 1-shot vaccines or 2 weeks after the second shot for 2-shot vaccines). The potential presence of such additional indicator (120) is preferred, as it would, for example, allow individuals to circulate without a mask, thus equating the device to a medical passport. Additionally, the pandemic wristband disclosed herein could be scanned also at airports to allow a third party to associate the green light to a specific name to be compared with the user's ID card or passport and provide a confirmation that the wearer is indeed free to travel.

In summary, according to an embodiment of the present disclosure, priority testing will be granted to the user in case light (115) is turned on or flashes. That light will stay on or flash in case the test results come back positive and will stay on until a) the user has met the required amount of time taken for the user to be free of the disease by just quarantining or b) meeting the required testing protocols for negative results showing a disease-free condition. On the other hand, light (120), whether in combination with the above procedure or not, will turn green to be used as a passport once immunity has been determined, for whatever length of time has been determined for the pandemic disease at issue.

If desired, the device according to the present disclosure can include a controllable lock or similar arrangement to prevent the device from being borrowed, stolen, lost or forgotten, thus providing a stronger reliability indicator also for places that do not require IDs, such as stores or sports gatherings. In particular, there are instances in which a removable wristband should be avoided as it could lead to a false sense of security and higher risk of infections if not worn at all times when around others.

The main body including the watch face (110) can also optionally include, on its top portion, a plurality of holes (105), e.g. three holes, for inclusion of medical alert charms or other types of charms such as cancer survivor, positive feeling, heart, USA charm and so on. Insertion of the charms can occur, for example, through a rubber band looping through the holes and then looping the charm.

In terms of initial distribution, the pandemic wristbands can be sent nationally or globally to every person by or on behalf of the U.S. or foreign government using, for example, census information. Alternatively or in addition, such devices may be distributed at testing sites, medical facilities, shelters, through the World Health Organization, and/or additional allocated locations decided upon within each state or nation/country.

It is likely that individuals belonging to different countries may be subject to different COVID-free or pandemic-free proof requirements. However, it is clear that proof of vaccination will soon become an important requirement of everyday life, not only nationally but also internationally. A possible way of implementation of the teachings of the present disclosure in the US (but it could equally apply to any country) could be that of requiring each individual travelling to the US to wear a US-regulated pandemic wristband as described herein for the duration of their stay in the US and be able to attend social events in the US as long as a green light is shown on their device.

According to an embodiment of the present disclosure, wristbands sent through the census will already have name and address of the user already downloaded and encoded through the QR code (135) together with an ID (140). The user will be able to add additional optional information by accessing a website indicated on the face in sections (125, 130). On the other hand, when distributed locally, the ID number (140) may be present, while the username and address can be added by scanning the QR code (135) at the local facility in order to add such information. Additional optional information can be added either at the facility or by accessing a web link, as noted above. The person skilled in the art will understand that other initialization and update procedures may be possible, the above examples just showing exemplary ways of how such procedures can be performed. By way of example, visibility of the ID number (140) may be controllable by hiding, coding, encrypting and/or similarly managing the ID to protect the user's privacy. Additionally, the ID number may be provided to the user separately from the wristband and/or an online access (possibly with a phone number if clarification is requested by the user) be provided for initialization and/or further use.

By way of example, each pandemic wristband will have a person's name, address and unique ID number downloaded in the built-in wristband processor and memory. Upon receipt, each person will be able to go online and add any pertinent information that will help save their life in the event they are infected with COVID-19 (or other kind of pandemic disease) and especially if unresponsive. Information such as phone number, medical issues, allergies, whether the individual previously tested positive or not, medication, emergency contact, number of family members, pets, insurance, occupation etc. will be optional and helpful to save the wearers and notify their family or emergency contact. In other words, only information individuals are willing to provide will be downloaded under an ID number. Such information will then be sent to the pandemic wristband and encoded into QR code (135) without any privacy risk, as it would instead occur in case a cell phone is used.

Figure 2:
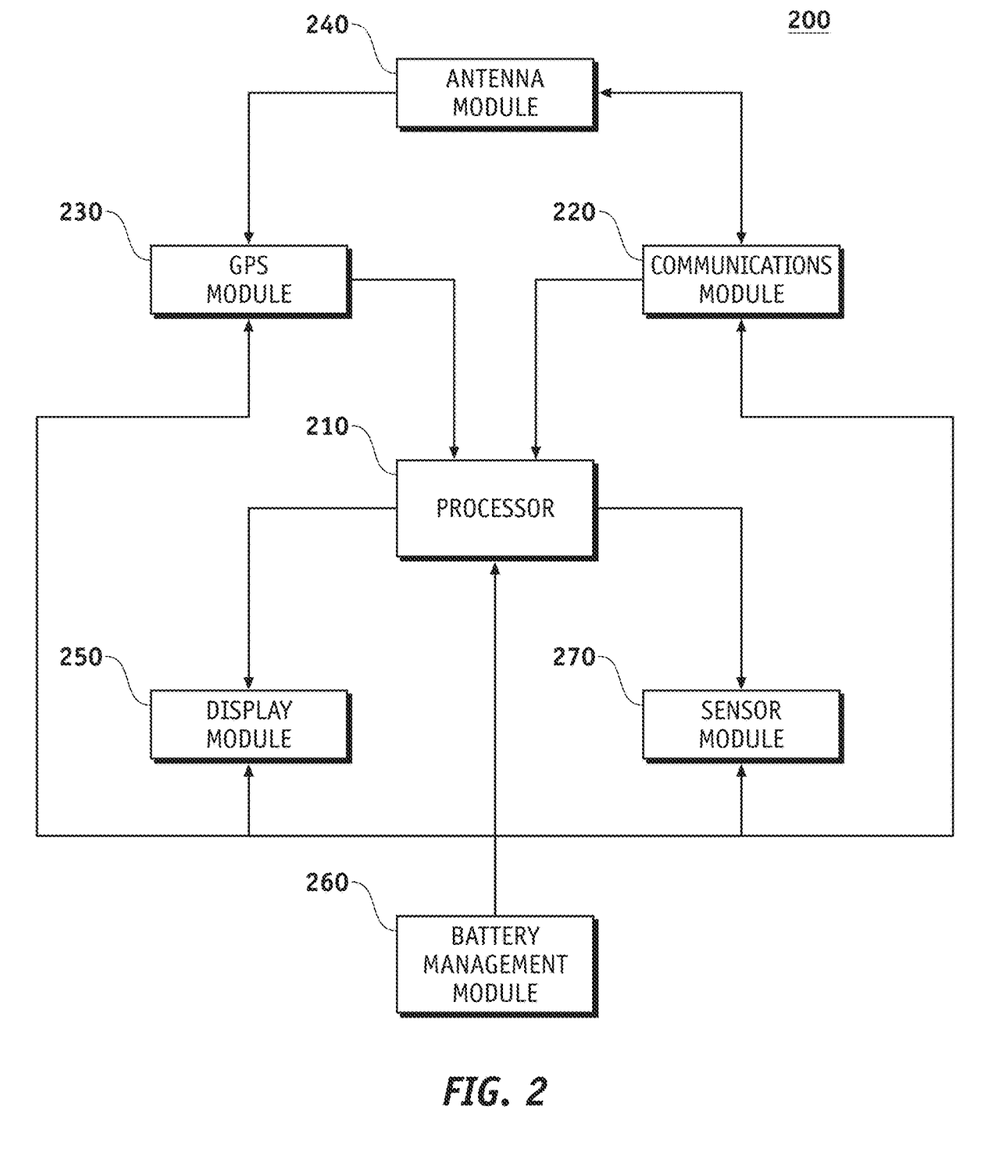
FIG. 2 shows an exemplary block diagram of a digital tracking and passport device according to an embodiment of the present disclosure.

FIG. 2 shows an exemplary block diagram of a digital tracking device (200) according to an embodiment of the present disclosure. Digital tracking device (200) comprises processor or controller (210), wireless communication module (220), GPS module (230), antenna module (240), display module (250), battery management module (260) and sensor module (270). Processor (210), although shown as a single module in the figure, may include one or more processors and memories, and control in general the functionality of the device by communicating with and providing control and command signals to various other modules. As an example, ARM® Cortex®-M class microprocessors may be used when implementing the controller/processor (210) although other types of microprocessors may also be envisaged by the person skilled in the art.

Communication of the device (200) with, for example, a repository or any other remote location to permit activation and/or deactivation of visual indicators (115) and/or (120) previously shown in FIG. 1, is performed through wireless communication module (220). By way of example, transfer of data may be performed through Transmission Control Protocol/Internet Protocol (TCP/IP) communication on a Code Division Multiple Access (CDMA) or Global System for Mobiles (GSM) network. Depending on the distance and location of the digital tracking device, other wireless protocols such as Wi-Fi® and/or Bluetooth® may also be implemented.

Figure 3:
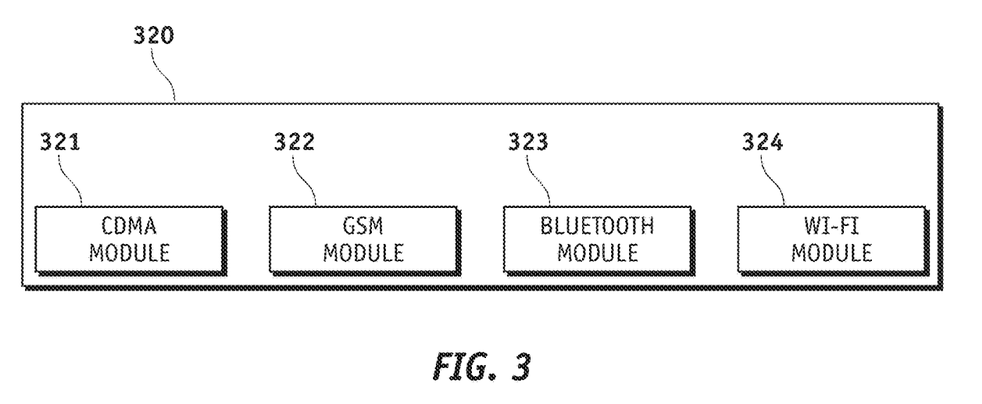
FIG. 3 shows an exemplary implementation of a wireless communication module described in FIG. 2.

If desired, the digital tracking device (200) of FIG. 2 may be connected with other devices. FIG. 3 shows an exemplary implementation of wireless communication module (220) of FIG. 2, indicated herein as (320), including CDMA module (321), GSM module (322), Bluetooth® module (323) and Wi-Fi® module (324). Depending on the application and requirements, one or more of the wireless modules (321, . . . , 324) may be implemented as part of the digital tracking device. Such modules may be integrated in a single chipset, or multiple wireless chipsets. The person skilled in the art will understand that if such connectivity is desired, it will have to fully respect the privacy concerns and issues discussed so far.

Referring back to FIG. 2, the location of the digital tracking devices is tracked by the global positioning system (GPS) module (230). Antenna module (240) may include one or more antennas coupled with GPS module (230), and one or more of the modules (321, . . . , 324) of FIG. 3 for data transmission and reception purposes. According to the teachings of the present disclosure the display module (250) of FIG. 2, one specific embodiment of which has been shown and discussed in FIG. 1, can include one or more of light emitting diode (LED), organic light-emitting diode (OLED), E-ink, traditional liquid crystal display (LCD), Sharp memory LCD, micro-electromechanical system (MEMS), or soft screen. The person skilled in the art will understand that other display technologies may also be considered when implementing the display module (250) of FIG. 2.

Figure 4:
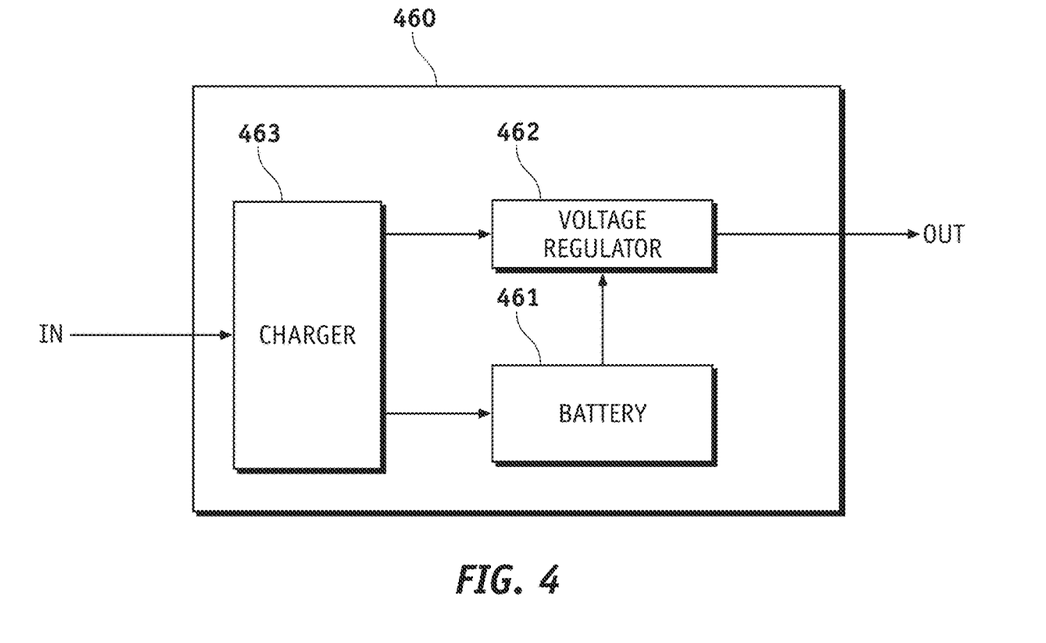
FIG. 4 shows an exemplary implementation of a battery management module described in FIG. 2.

With continued reference to FIG. 2, the battery management module (260) supplies the required power to various electronic modules within the digital tracking device (200), also depending on whether the wristband is permanently locked like a hospital band until cut off or is removable instead. FIG. 4 shows an exemplary implementation of battery management module (260), indicated herein as (460), including battery (461), voltage regulator (462) and charger (463). The voltage of battery (461) is regulated by voltage regulator (462) to generate a regulated supply voltage at the output (OUT) coupled to other electronic modules. The battery charger (463) receives input (IN) through, for example, a mini-USB connection which can be connected to a device with USB connection such as a laptop. The battery charger (463) may also be wall-plugged in another implementation. Battery (461) may include, for example, Li-ion and Lithium polymer batteries. Voltage regulator (462) may include, for example, a low-dropout (LDO) regulator.

Figure 5:
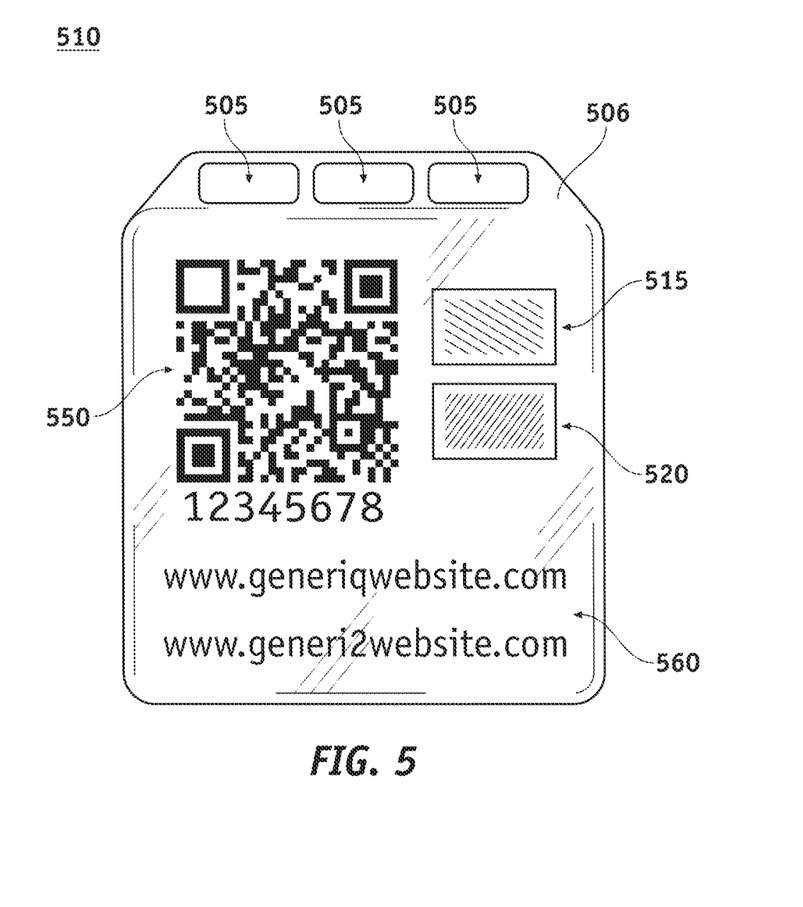
FIG. 5 shows an exemplary layout of the watch face of FIG. 1.

FIG. 5 shows an example layout for the watch face (510) of the device. The face (510) can include a display screen (550) for displaying the QR code and identification information (number, name, etc.). The red (515) and green (520) indicator lights are also present on the face (510). In some embodiments, the lights are combined into a single light that is capable of changing color between at least red and green. The lights can be provided by, for example, light emitting diodes or other similar small illuminating devices. The lights can be colored lights, or white lights shown through a color filter. In some embodiments, the lights are virtual lights shown on the display screen (550). An area (560) of the watch face (510) can be reserved to display other information, such as website information, identifying logos, or designs specific to the organization providing the watch. The information can be drawn or etched on the watch face (510) or be shown on a digital screen, either separate from or a part of the main digital screen (550). In the embodiment where the information is on a digital screen, showing the information can be triggered by activation of the red indicator light. Charm loop holes (505) can be placed in the watch face (510). In some embodiments, the holes (505) are on a beveled portion (506) of the face. The layout provided in FIG. 5 is just an example: the various parts (505, 506, 515, 520, 550, 560) can be placed in different arrangements and with different relative sizes and shapes.

While an embodiment of the present disclosure has been shown with a digital display screen, additional embodiments of the present disclosure are also possible with light indicators (having the same functions as described above) and a QR code not necessary part of a digital screen. Additionally, further embodiments can also be provided where a single light indicator is present, having the ability of being illuminated to show a solid or flashing red color or a green color.

With reference to FIGS. 1 and 2, digital device (200) as disclosed, is mainly used for COVID (and any other pandemics) prevention, tracking and passport purposes. However, the person skilled in the art will appreciate that other functionalities, including but not limited to those that can be found in smart watches, fitness trackers, and health monitoring devices may also be implemented as part of the design. As such, and in line with future technology improvements, sensor module (270) can be optionally implemented to potentially, but not necessarily, include a) heart rate and oxygen saturation level sensors, b) motion sensors such as acceleration, gyroscope, geomagnetic, and atmospheric pressure sensors, c) additional biosensors such as glucose, blood pressure, ECG, EMG, temperature and brain wave sensors, and/or d) temperature and humidity, gas, PH, ultraviolet, ambient light, dust particles, and pressure sensors. It is appreciated that, without impacting the main application of the disclosed digital tracking device, inclusion of one or more such sensors will broaden the usage and applications of the device.

Turning now to the general teachings of the present disclosure, it should be noted that in the only information that is not user-provided is their name and address. All other information can be provided at the user's discretion and control and can also be changed in time. In this way, any privacy concerns are well addressed and customized on a user-by-user basis.

Given that the effectiveness of the tracking, tracing and contacting system described in the present application is a function of the number of users wearing the pandemic wristband, use of such wristband may become mandatory before a COVID-19 (or other kind of pandemic) test is administered if so desired by a local and/or federal authority.

The teachings of the present disclosure will allow the use of a coordinated statewide, national, and global plan to help in Phase 4 (i.e. when shutdown will be lifted) and to help the pandemic through tracking, tracing, contacting and passport indication to show immunity. The device according to the present disclosure provides a non-discriminating way to help everyone as it is configured to reach everyone equally and can give priority testing equally.

As already noted in several sections of the present disclosure, while the use of the present pandemic wristband is currently targeted with reference to COVID-19, the person skilled in the art will understand that the wristband may be used for any type of pandemics.

The invention claimed is:

1. A method to track an individual wearing a battery-operated wearable and lockable tracking device, the battery-operated wearable and lockable tracking device comprising:
 a lockable wristband;
 a main body connected to the wristband and including an area configured to show medical alert charms;
 a location tracker in the main body configured to transmit device location of the wearable and lockable tracking device;
 a processor in the main body configured to process and wirelessly receive notification of a condition based on the wearable and lockable tracking device location transmitted by the location tracker; and
 a battery,
the method comprising:
 providing, on the wearable and lockable tracking device or separately from the wearable and lockable tracking device, an identification number uniquely identifying the wearable and lockable tracking device;
 storing the identification number remotely of the wearable and lockable tracking device;
 receiving, from the location tracker, device location information about the wearable and lockable tracking device;
 based on the location information received, determining whether the individual is potentially subject to the condition;
 in case the individual is potentially subject to the condition, tracking the device location and wirelessly alerting the individual wearing the wearable and lockable tracking device;
 tracking the individual; and
 upon tracking of the individual, identifying the individual wearing the wearable and lockable tracking device.

2. The method of claim 1, wherein the battery-operated wearable and lockable tracking device is configured to reveal, upon scanning, personal information about the individual.

3. The method of claim 2, wherein said identifying occurs by revealing said personal information.

4. The method of claim 1, wherein the wirelessly alerting the individual comprises activating an indicator light on the main body of the wearable and lockable tracking device.

5. The method of claim 4, wherein the indicator light is a red light.

6. The method of claim 4, wherein the indicator light is a solid light or a flashing light.

7. The method of claim 4, wherein the indicator light is on a display screen of the main body.

8. The method of claim 7, wherein the display screen is configured to display one or more web links to the individual.

9. The method of claim 1, wherein the wearable and lockable tracking device is a waterproof device.

10. The method of claim 1, wherein the area configured to show medical alert charms includes one or more holes for hosting the charms, the charms being insertable by the individual.

11. The method of claim 1, wherein the location tracker is a global positioning system (GPS) location tracker.

12. The method of claim 1, wherein the wirelessly alerting the individual comprises activating a vibrating arrangement on the main body of the wearable and lockable tracking device.

13. The method of claim 4, further comprising a vibrating arrangement on the main body of the wearable and lockable tracking device.

14. The method of claim 2, wherein the battery-operated wearable and lockable tracking device is configured to reveal additional information about the individual inserted directly by the individual upon initial activation and later added or edited if needed.

* * * * *